United States Patent
Cho et al.

(10) Patent No.: US 12,169,926 B2
(45) Date of Patent: Dec. 17, 2024

(54) SYSTEM AND METHOD FOR DISEASE DIAGNOSIS USING NEURAL NETWORK

(71) Applicant: DEEP BIO INC., Seoul (KR)

(72) Inventors: Joon Young Cho, Seoul (KR); Sun Woo Kim, Seongnam-si (KR)

(73) Assignee: DEEP BIO INC., Seoul (KR)

( * ) Notice: Subject to any disclaimer, the term of this patent is extended or adjusted under 35 U.S.C. 154(b) by 721 days.

(21) Appl. No.: 17/266,090

(22) PCT Filed: Aug. 7, 2019

(86) PCT No.: PCT/KR2019/009844
§ 371 (c)(1),
(2) Date: Feb. 4, 2021

(87) PCT Pub. No.: WO2020/032559
PCT Pub. Date: Feb. 13, 2020

(65) Prior Publication Data
US 2021/0304405 A1    Sep. 30, 2021

(30) Foreign Application Priority Data

Aug. 7, 2018 (KR) .......... 10-2018-0092011

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/7264* (2013.01); *G06N 3/045* (2023.01);
(Continued)

(58) Field of Classification Search
CPC ........ G06T 7/0012; G06T 2207/10024; G06T 2207/20021; G06T 2207/20076;
(Continued)

(56) References Cited

U.S. PATENT DOCUMENTS

2014/0233826 A1    8/2014 Agaian et al.
2016/0358069 A1    12/2016 Brothers et al.
(Continued)

FOREIGN PATENT DOCUMENTS

CN    108230257    *    6/2018
KR    10-1590483         6/2015
(Continued)

OTHER PUBLICATIONS

Mosquera-Lopez et al., "Computer-Aided Prostate Cancer Diagnosis From Digitized Histopathology: A Review on Texture-Based Systems", IEEE Reviews in Biomedical Engineering, vol. 8, 2015 (Year: 2015).*
(Continued)

*Primary Examiner* — Qian Yang
(74) *Attorney, Agent, or Firm* — PnK IP LLC

(57) ABSTRACT

A system for disease diagnosis includes a patch neural network for generating a patch-level diagnostic result of whether or not a disease is present in each of predetermined patches formed by dividing a slide into a predetermined size; a heat map generation module for generating a patch-level heat map image corresponding to the biometric image obtained from the slide on the basis of the patch diagnostic results of the respective multiple patches included in the slide; a tissue mask generation module for generating a tissue mask image corresponding to the biometric image obtained from the slide on the basis of a hue-saturation-value (HSV) model corresponding to the slide; and a visualization module for generating a disease diagnostic visualization image corresponding to the biometric image obtained from the slide on the basis of the patch-level heat map image and the tissue mask image.

17 Claims, 10 Drawing Sheets

(51) Int. Cl.
  *G06N 3/045* (2023.01)
  *G16H 30/40* (2018.01)
  *G16H 50/20* (2018.01)
  *G16H 50/30* (2018.01)
(52) U.S. Cl.
  CPC ............. *G16H 30/40* (2018.01); *G16H 50/20* (2018.01); *G16H 50/30* (2018.01)
(58) Field of Classification Search
  CPC . G06T 2207/20081; G06T 2207/20084; G06T 2207/30024; G06T 2207/30081; G06T 2207/30096; A61B 5/7264; A61B 5/0075; A61B 5/4381; A61B 5/4842; A61B 5/7267; G06N 3/045; G16H 30/40; G16H 50/20; G16H 50/30
  See application file for complete search history.

(56) References Cited

U.S. PATENT DOCUMENTS

| | | | |
|---|---|---|---|
| 2017/0053398 A1* | 2/2017 | Mahoor | ................... G06T 7/42 |
| 2017/0215728 A1* | 8/2017 | Wen | ................... A61B 3/0025 |
| 2018/0114317 A1 | 4/2018 | Song et al. | |
| 2018/0268256 A1* | 9/2018 | Di Febbo | ............. G06V 10/757 |
| 2019/0385306 A1 | 12/2019 | Kim | |

FOREIGN PATENT DOCUMENTS

| | | |
|---|---|---|
| KR | 10-2016-0034814 | 3/2016 |
| KR | 10-2016-0142791 | 12/2016 |
| KR | 10-2016-0168176 | 6/2018 |
| KR | 10-2018-0066983 | 6/2018 |
| WO | WO 2017/200524 | * 11/2017 |

OTHER PUBLICATIONS

Chung et al., "Prostate Cancer Detection via a Quantitative Radiomics-Driven Conditional Random Field Framework", Digital Object Identifier 10.1109/ACCESS.2015.2502220 (Year: 2015).*
Machine translation for CN 108230257 (Year: 2018).*
International Search Report mailed Jan. 28, 2020, issued in International Application No. PCT/KR2019/009844 (with English Translation).

* cited by examiner

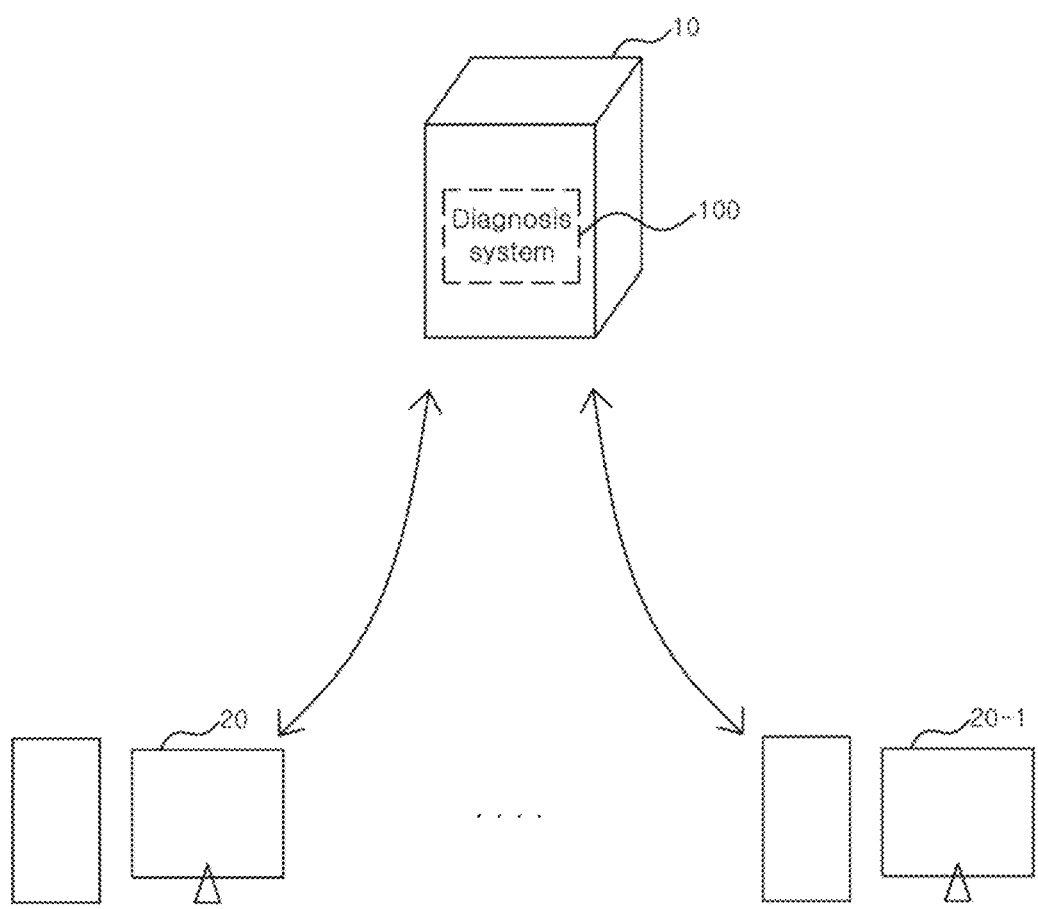

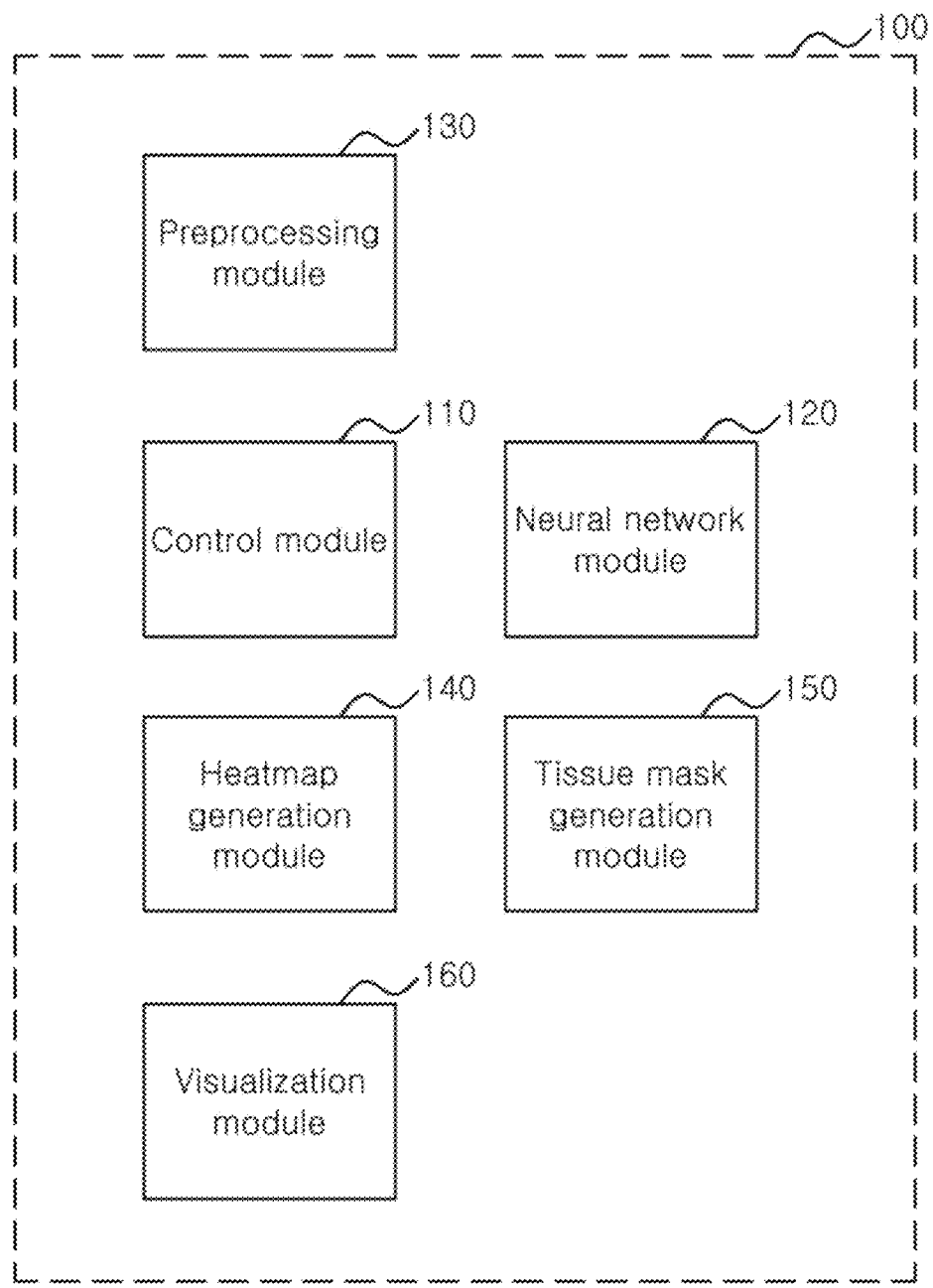

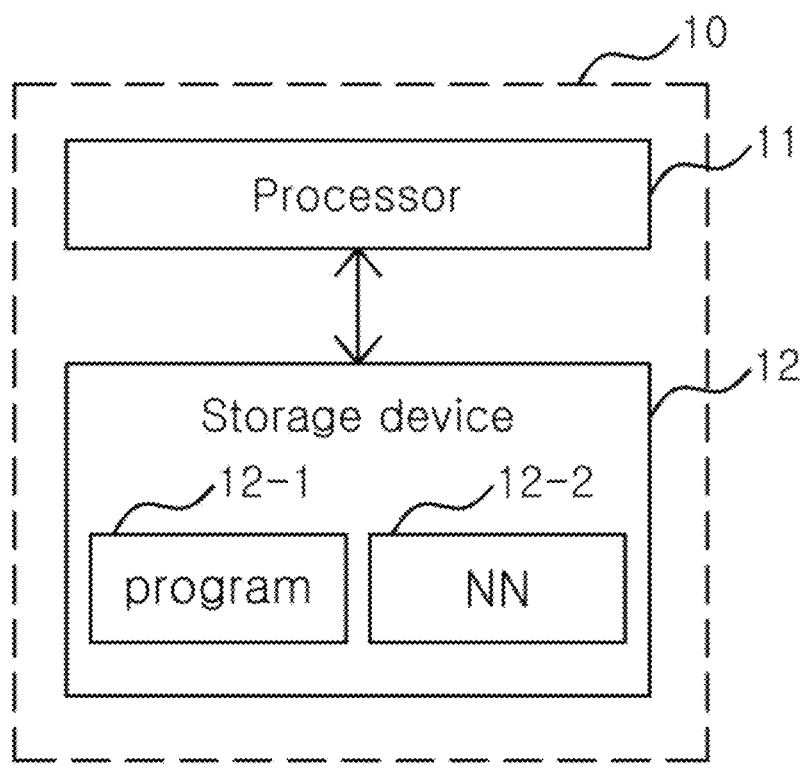

SYSTEM AND METHOD FOR DISEASE
DIAGNOSIS USING NEURAL NETWORK

CROSS REFERENCE TO RELATED
APPLICATION

This application is a National Stage Entry of International Application No. PCT/KR2019/009844, filed on Aug. 7, 2019, and claims priority from and the benefit of Korean Patent Application No. 10-2018-0092011, filed on Aug. 7, 2018, each of which is hereby incorporated by reference for all purposes as if fully set forth herein.

TECHNICAL FIELD

The present invention relates to a disease diagnosis system using a neural network and a method thereof. More specifically, the present invention relates to a system and method which can diagnose a predetermined disease (e.g., prostate cancer), when an image of a biological tissue is input, by performing learning through a neural network and using the learned neural network, and visualize a tissue part diagnosed as a disease to accurately locate the tissue part.

DISCUSSION OF THE BACKGROUND

One of major tasks performed by pathology or a pathology department is to read a patient's biometric image and perform diagnosis for determining a state or symptom of a specific disease. Performing such a diagnosis like this requires a method that depends on the experience and knowledge of medical personnel skilled for an extended period of time.

Recently, attempts of automating the tasks such as recognizing or classifying images using a computer system have been made owing to advancement in machine learning. Particularly, attempts have been made to automate diagnosis performed by skilled medical personnel using a neural network (e.g., a deep learning method using a convolution neural network (CNN)), which is a kind of machine learning.

Particularly, diagnosis through deep learning using a neural network (e.g., CNN) sometimes finds out characteristics of disease factors unknown to experienced medical personnel from an image in that it does not simply automate the experience and knowledge of the experienced medical personnel, but finds out characteristic factors through self-learning and derives a desired answer.

Generally, diagnosis of a disease through a neural network using a biometric image uses a piece of biometric image, i.e., a patch (or also referred to as a tile) obtained from a biological sample provided on a slide. That is, a skilled medical practitioner annotates the state of a specific disease (e.g., whether cancer is expressed) with regard to a corresponding tile, and trains the neural network using a plurality of annotated tiles as training data. In this case, a convolution neural network may be used as the neural network.

However, in this method, the trained neural network determines the state of a disease of a corresponding tile on the basis of image features of the tile. In practice, when the state of a specific biological tissue is determined for a specific disease, there are cases in which even the current state of the tissues around a specific biological tissue (e.g., the shape, whether a specific pattern exists, etc.) should be considered, in addition to the specific biological tissue itself. However, there is a problem in that the conventional method is not suitable in this case.

Meanwhile, in the conventional learning method, the color itself of a biometric image or a patch is input as an input data. That is, in general, an input data defined by three channel values of Red, Green and Blue (RGB) is used as it is.

However, in this case, the color of a tissue being dyed may be different according to the characteristics of a dyeing reagent used for dyeing a biological tissue corresponding to the biometric image, and this may directly affect a trained neural network.

Accordingly, a neural network needs to be trained in a manner more robust to non-fundamental color features according to dyeing or the like, which are not the fundamental image features of a tissue.

In addition, when whether a disease is expressed is determined for each patch according to a result of diagnosis by the patch unit and the result of diagnosis by the patch unit is visualized immediately, there may be a problem in that parts other than the tissue are visualized in practice. Accordingly, a visualization method may be needed to clearly identify a part of tissue diagnosed as a disease.

SUMMARY

Therefore, the present invention has been made in view of the above problems, and an aspect of the invention provides a diagnosis system using a neural network and a method thereof, which can further increase accuracy by using even surrounding tiles, as well as a specific tile, for learning in order to determine a state of disease of the specific tile (e.g., whether or not a disease is expressed, or an index indicating the state of a disease).

In addition, another aspect of the invention provides a diagnosis system using a neural network and a method thereof, which may have a characteristic robust to color, not the image features fundamental to diagnosing whether or not a disease is expressed.

In addition, another aspect of the invention provides a visualization method for clearly identifying a tissue part where a disease is expressed, and a diagnosis system using a neural network, which can perform the method.

To accomplish the above aspects, according to one embodiment, there is provided a disease diagnosis system implemented in a system including a processor and a storage device for storing a neural network, and using a slide having biological tissue provided thereon from which is a biometric image is obtained, and the neural network, the diagnosis system including: a patch neural network configured to generate a patch-level diagnosis result indicating whether a disease exists in each of predetermined patches generated by dividing the biometic image obtained from the slide in a predetermined size; a heatmap generation module configured to generate a patch-level heatmap image corresponding to the slide on the basis of the patch-level diagnosis result of each of the plurality of patches included in the biometric image obtained from the slide; a tissue mask generation module configured to generate a tissue mask image corresponding to the biometric image obtained from the slide on the basis of a hue-saturation-value (HSV) model corresponding to the biometric image obtained from the slide; and a visualization module configured to generate a disease diagnosis visualization image corresponding to the biometric image obtained from the slide on the basis of the patch-level heatmap image and the tissue mask image.

In an embodiment, the tissue mask generation module may generate a first binarization result by performing image binarization on an S space corresponding to the biometric image obtained from the slide (here, the S space corresponding to the slide is a saturation space of an HSV model corresponding to the slide), generate a second binarization result by performing image binarization on a 1-V space corresponding to the biometric image obtained from the slide (here, the V space corresponding to the biometric image obtained from the slide is a brightness value space of an HSV model corresponding to the biometric image obtained from the slide), and generate a tissue mask image corresponding to the biometric image obtained from the slide on the basis of the first binarization result and the second binarization result.

In an embodiment, the first binarization result and the second binarization result may include a binary value corresponding to each pixel of the biometric image obtained from the slide (here, the binary value is 0 or 1), and for each pixel of the biometric image obtained from the slide, the tissue mask generation module may determine a pixel of a tissue mask image corresponding to the pixel as a tissue pixel when the binary value of the first binarization result corresponding to the pixel or the binary value of the second binarization result corresponding to the pixel is 1, and determine the pixel of the tissue mask image corresponding to the pixel as a non-tissue pixel otherwise.

In an embodiment, the visualization module may generate a disease diagnosis visualization image corresponding to the biometric image obtained from the slide by applying a Conditional Random Field to the patch-level heatmap image and the tissue mask image.

In an embodiment, in the conditional random field, the number of labels may be 2, and pixels equal to or smaller than a specific threshold among the pixels included in the patch-level heatmap image may be converted to 0.

In an embodiment, the disease may be prostate cancer.

According to another aspect of the present invention, there is provided a method performed by a disease diagnosis system implemented in a system including a processor and a storage device and using a biometric image and a neural network, the method comprising: a diagnosis step of generating a patch-level diagnosis result indicating whether a disease exists in each of predetermined patches generated by dividing a biometric image obtained from the slide in a predetermined size using the neural network, by the diagnosis system; a heatmap generation step of generating a patch-level heatmap image corresponding to the biometric image obtained from the slide on the basis of the patch-level diagnosis result of each of the plurality of patches included in the biometric image obtained from the slide, by the diagnosis system; a tissue mask generation step of generating a tissue mask image corresponding to the biometric image obtained from the slide on the basis of a hue-saturation-value (HSV) model corresponding to the biometric image obtained from the slide, by the diagnosis system; and a visualization step of generating a disease diagnosis visualization image corresponding to the biometric image obtained from the slide on the basis of the patch-level heatmap image and the tissue mask image, by the diagnosis system.

In an embodiment, the tissue mask generation step may include the steps of: generating a first binarization result by performing image binarization on an S space corresponding to the biometric image obtained from the slide (here, the S space corresponding to the biometric image obtained from the slide is a saturation space of an HSV model corresponding to the slide); generating a second binarization result by performing image binarization on a 1-V space corresponding to the biometric image obtained from the slide (here, the V space corresponding to the biometric image obtained from the slide is a brightness value space of an HSV model corresponding to the biometric image obtained from the slide); and generating a tissue mask image corresponding to the biometric image obtained from the slide on the basis of the first binarization result and the second binarization result.

In an embodiment, the first binarization result and the second binarization result may include a binary value corresponding to each pixel of the biometric image obtained from the slide (here, the binary value is 0 or 1), and the step of generating a tissue mask image corresponding to the biometric image obtained from the slide on the basis of the first binarization result and the second binarization result may include the step of determining, for each pixel of the biometric image obtained from the slide, a pixel of a tissue mask image corresponding to the pixel as a tissue pixel when the binary value of the first binarization result corresponding to the pixel or the binary value of the second binarization result corresponding to the pixel is 1, and determining the pixel of the tissue mask image corresponding to the pixel as a non-tissue pixel otherwise.

In an embodiment, the visualization step may include the step of generating a disease diagnosis visualization image corresponding to the biometric image obtained from the slide by applying a Conditional Random Field to the patch-level heatmap image and the tissue mask image.

In an embodiment, in the conditional random field, the number of labels may be 2, and pixels equal to or smaller than a specific threshold among the pixels included in the patch-level heatmap image may be converted to 0.

According to another aspect of the present invention, there is provided a computer program installed in a data processing device and recorded in a medium for performing the method described above.

According to one or more embodiments of the invention, since there is provided a neural network which can determine a disease state of a specific patch considering a macro patch including the specific patch and further including surrounding patches while performing diagnosis on the specific patch, there is an effect of providing a higher diagnosis accuracy.

According to one or more embodiments of the invention, as a gray channel, as well as an input data, i.e., the original color value of a patch (e.g., RGB 3 channel values), is additionally used as an input data, there is an effect of having a characteristic robust to variations according to various factors of color, not the image features fundamental to diagnosing whether a disease is expressed, while preventing a situation of ignoring image features related to a disease expressed by a color difference that may occur when only the gray channel is simply used.

In addition, according to the spirit of the present invention, there is an effect of separately visualizing only a tissue part within a patch determined as expressing a disease.

BRIEF DESCRIPTION OF THE DRAWINGS

To more sufficiently understand the drawings cited in the detailed description of the present invention, a brief description of each drawing is provided.

FIG. 1 is a view showing a schematic system configuration of a disease diagnosis system using a neural network constructed according to principles of the invention.

FIG. 2 is a view showing a logical configuration of a disease diagnosis system using a neural network according to an embodiment.

FIG. 3 is a view showing a hardware configuration of a disease diagnosis system using a neural network according to an embodiment.

DETAILED DESCRIPTION

Figure 4A:
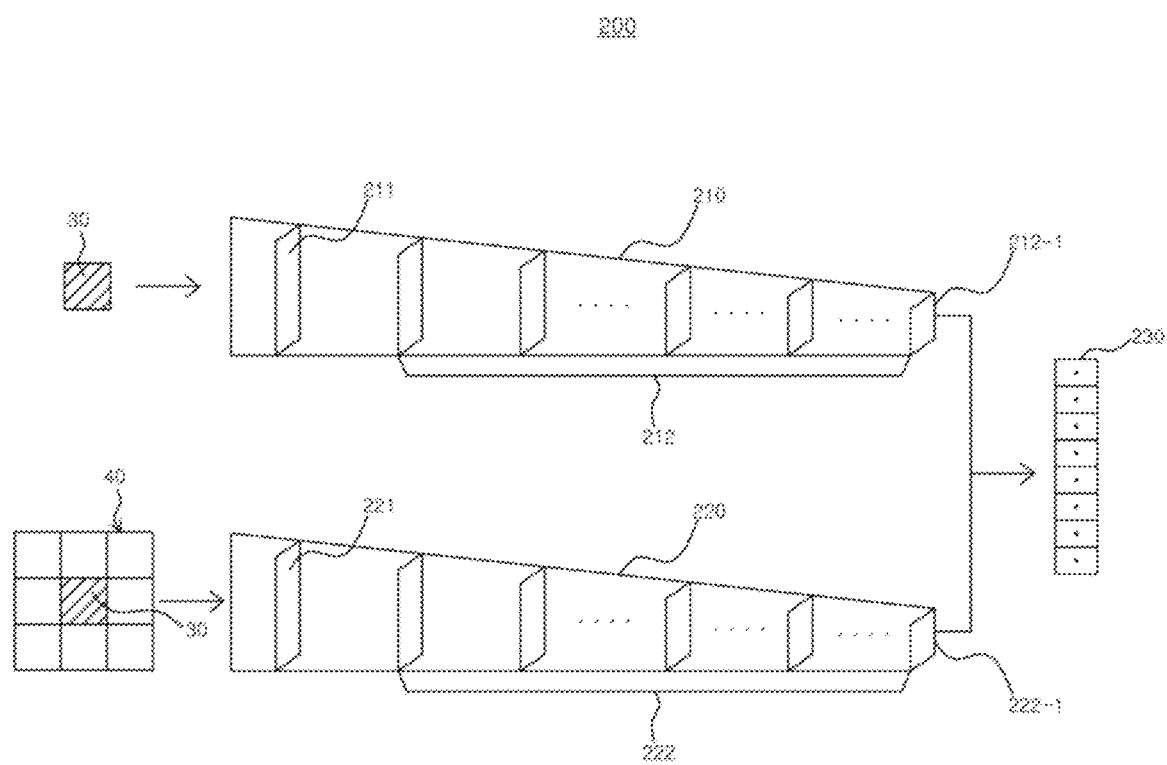
FIGS. 4A and 4B are views showing an exemplary configuration of a neural network according to an embodiment.

As the present invention may apply various modifications and have various embodiments, specific embodiments will be illustrated in the drawings and described in detail in the detailed description. However, this is not intended to limit the present invention to the specific embodiments, and it should be understood to include all modifications, equivalents, and substitutes included in the spirit and scope of the present invention. In describing the present invention, when it is determined that detailed description of a related known technology may obscure the subject matter of the present invention, the detailed description will be omitted.

Although the terms such as first, second and the like may be used to describe various components, the components should not be limited by the terms. These terms are only used for the purpose of distinguishing one component from the other components.

The terms used in the present application are only used to describe specific embodiments, and are not intended to limit the present invention. Singular expressions include plural expressions unless the context clearly indicates otherwise.

In this specification, the terms such as "comprise" or "have" are intended to designate the presence of features, numbers, steps, actions, components, parts, or combinations thereof described in the specification, and it is to be understood that they do not preclude the possibility of the presence or addition of one or more other features or numbers, steps, actions, components, parts, or combinations thereof.

In addition, in this specification, when any one component 'transmits' data to another component, this means that the component may directly transmit the data to another component, or may transmit the data to another component through at least one other component. On the contrary, when one component 'directly transmits' data to another component, it means that the data is transmitted from the component to another component without passing through the other components.

Hereinafter, the present invention will be described in detail focusing on the embodiments of the present invention with reference to the accompanying drawings. The same reference numerals in each drawing indicate the same members.

FIG. 1 is a view showing a schematic system configuration of a disease diagnosis system using a neural network constructed according to principles of the invention.

Referring to FIG. 1, a disease diagnosis system 100 (hereinafter, a diagnosis system) using a neural network constructed according to principles of the invention may be installed in a predetermined server 10 to implement one or more embodiments described in detail hereinbelow. The server 10 corresponds to a data processing device having a computing ability for implementing one or more embodiments of the invention, and those skilled in the art may easily infer that any device capable of performing a specific service such as a personal computer, a portable terminal or the like, as well as a data processing device that can be generally accessed by a client through a network, may be defined as a server.

The server 10 may include a processor 11 and a storage device 12 as shown in FIG. 3. The processor 11 may correspond to a computing device capable of driving a program 12-1 for implementing one or more embodiments, and the processor 11 may perform diagnosis using the program 12-1 and a neural network 12-2. The neural network 12-2 may include a patch neural network that performs patch-level diagnosis as described below.

The storage device 12 may correspond to a data storage unit capable of storing the program 12-1 and the neural network 12-2, and may be implemented as a plurality of storage units according to implementation examples. In addition, the storage device 12 may correspond to a temporary storage device or a memory that may be included in the processor 11, as well as a main memory device or the like included in the server 10.

Although it is shown in FIG. 1 or 3 that the diagnosis system 100 is implemented as any one physical device, those skilled in the art may easily infer that the diagnosis system 100 according to embodiments of the invention may be implemented by organically combining a plurality of physical devices as needed.

In this specification, when it is described that the diagnosis system 100 performs diagnosis, it may denote a series of processes for receiving a biometric image expressing a biological tissue, i.e., the entire slide or a patch that is a part of the slide, and outputting an output data defined in this specification.

According to an embodiment, the diagnosis system 100 may perform patch-level diagnosis. The patch-level diagnosis may denote dividing a biometric image obtained from biological tissue provided on the slide into patches and diagnosing whether or not a disease is expressed in the divided patches. Accordingly, the diagnosis system 100 may receive an input for each patch of the slide and output whether or not a disease is expressed in a corresponding patch. It goes without saying that a neural network for this purpose may be training to implement the diagnosis system 100.

Meanwhile, according to an embodiment, the neural network performing the patch-level diagnosis may perform diagnosis by further considering surrounding patches of a corresponding patch, rather than performing diagnosis using only the corresponding patch. Such neural network performing like this has been disclosed in detail in the Korean patent application filed by the applicant (application number 10-2016-0168176, a system and method for diagnosing disease using a neural network, hereinafter referred to as 'previous application'). Through the previous application, accuracy of diagnosis may be improved when the surrounding areas are considered together, rather than when the diagnosis is performed considering only a very narrow area, i.e., an area corresponding to the patch. Furthermore, according to one or more embodiments of the invention, there is an effect of more accurately determining whether a disease exists in biological tissue provided on the slide by further considering physical characteristics such as the location, density, and cluster size of patches in the entire slide, in addition to those of surrounding patches of a specific patch. The previous application is included as a reference of the present invention, and contents thereof may be regarded as being described in this specification.

Meanwhile, state information output by the patch-level diagnosis may be information indicating a probability of whether a specific disease (e.g., cancer of a specific type) is expressed in a tissue corresponding to the patch. When a probability of greater than or equal to a specific reference value (threshold value) appears, the diagnosis system 100 may determine the patch as a patch in which a disease (e.g., prostate cancer) is expressed.

Of course, the diagnosis system 100 may provide information indicating a degree of progression of a specific disease (or a probability corresponding to the degree of progression), as well as whether or not a specific disease is expressed, as disclosed in the previous application. For example, when one or more embodiments of the invention are used for diagnosis of prostate cancer, the Gleason Pattern or Gleason Score, which are indexes indicating a degree of progression of prostate cancer, may be included in the state information output from the neural network. For example, the Gleason score has a value of 2 to 5, and a larger number indicates a higher degree of expression of the prostate cancer. Accordingly, the state information may denote a probability that a biological tissue corresponding to a patch to be diagnosed corresponds to a specific value (e.g., 3, 4 or 5) of the Gleason score.

There may be a plurality of state information that are used in one or more embodiments. For example, first state information may indicate a probability of the Gleason score for being 3, second state information may indicate a probability of the Gleason score for being 4, and third state information may indicate a probability of the Gleason score for being 5, and all state channels corresponding to the first state information, the second state information, and the third state information may be defined in an output layer. According to implementations, state information indicating a probability that the Gleason score has a predetermined range (e.g., 3 to 5, 4 to 5, etc.) may be defined. That is, one piece of state information may correspond to a plurality of indexes expressing a state of progression of a disease.

In this case, the neural network may determine that the patch is a disease patch, i.e., a disease-expressed patch, when the state information having a Gleason score of 3 or more is equal to or greater than a predetermined threshold value.

Meanwhile, the threshold value used by the neural network may be set variously. According to one or more embodiments, a plurality of threshold values may be used. It goes without saying that a specific patch may be determined as a disease-expressed patch, i.e., a disease patch, or a normal patch according to the threshold value.

According to one or more embodiments of the invention, there may be a plurality of threshold values used by the neural network, and in this case, a disease patch diagnosed according to each of the plurality of threshold values may vary.

Meanwhile, the diagnosis system 100 may perform visualization on a result of the performed patch-level diagnosis. As described herein, visualization of a diagnosis result may mean giving a predetermined visual effect to a part determined as a disease as a result of a diagnosis. The visual effect may denote an effect that can be perceived by sight. For example, a part determined as a disease by visualization may be expressed or emphasized in a different color.

When the diagnosis system 100 is implemented to be included in a predetermined server 10, the diagnosis system 100 may perform communication with at least one client (e.g., 20, 20-1) accessible to the server 10. In this case, the client (e.g., 20, 20-1) may transmit a biometric image to the diagnosis system 100, and the diagnosis system 100 may perform diagnosis on the transmitted biometric image according to the spirit of the present invention. In addition, the diagnosis system 100 may transmit a diagnosis result to the client (e.g., 20, 20-1).

The diagnosis system 100 may perform patch-level diagnosis using a neural network according to one or more embodiments of the invention. Of course, a process of training the neural network may be performed first to perform the diagnosis.

Accordingly, the diagnosis system 100 may be a system that receives a neural network trained according to one or more embodiments of the invention and a program for performing diagnosis using the neural network from the outside and performs diagnosis, or it may be a system that performs even the training. In addition, the diagnosis system 100 may be implemented as a dedicated device manufactured to implement one or more embodiments of the invention, not a general-purpose data processing device. In this case, a component for scanning biometric images may be further provided.

As disclosed in the previous application, the neural network may have a characteristic of performing diagnosis on a specific patch considering not only an image of the specific patch itself to perform diagnosis on the specific patch, but also considering even an image of at least one adjacent patch of the specific patch. Through such a system like this, there is an effect of improving accuracy to a very meaningful level in diagnosing a disease that should consider not only the biological tissue but also the state of surrounding tissues of the biological tissue to actually diagnose a biological tissue corresponding to a specific patch. In addition, when a biometric image is divided into a plurality of patches, there is a strong effect on the influence of a diagnosis result that may occur depending on the method of dividing patches or the location of a divided area in the biological tissue.

Of course, as described above, the neural network may not have the features disclosed in the previous application, and in any case, the neural network may be a neural network that is trained to perform diagnosis for each patch.

At this point, unlike what is described in the previous application, the neural network may further receive an additional channel as an input value for each of pixels included in the patch. The additional channel may be a gray value of each pixel. Accordingly, the neural network may further receive a gray channel, which is an additional channel, as an input in addition to 3 channels of original values (e.g., RGB) of the pixels included in the patch while receiving an input for each patch.

In this case, it may have a strong effect when the color of a biometric image changes due to a factor (e.g., characteristics of a diagnosis institution, dyeing reagent, etc.) unrelated to image features related to a disease. Of course, there may be a problem in that such important information is not reflected in learning when image features related to a disease are reflected in color and displayed, which may occur when only the gray channel is used rather than simply using an original value, and this problem may be solved.

The neural network used by the diagnosis system 100 according to one or more embodiments of the invention may include a micro neural network and a macro neural network.

The micro neural network may denote a network that performs learning using a specific tile and performs a series of processes for performing diagnosis on the tile using the image features of the tile itself.

The macro neural network may denote a network that performs learning using not only the tile but also a macro tile including the tile and at least one adjacent tile of the tile, and performs a series of processes for performing diagnosis on the tile using image features of the entire macro tile.

Therefore, the neural network according to one or more embodiments of the invention may have a characteristic of performing diagnosis on a specific tile considering not only an image of the specific tile itself to perform diagnosis on the specific tile, but also considering even an image of at least one adjacent tile of the specific tile. Through the use of a neural network like this, there is an effect of improving accuracy to a very meaningful level in diagnosing a disease that should consider not only the biological tissue but also the state of surrounding tissues of the biological tissue to actually diagnose a biological tissue corresponding to a specific tile. In addition, when a biometric image is divided into a plurality of tiles, there is a strong effect on the influence of a diagnosis result that may occur depending on the method of dividing tiles or the location of a divided area in the biological tissue.

The diagnosis system 100 for implementing one or more embodiments may have a configuration logically the same as shown in FIG. 2.

FIG. 2 is a view showing a logical configuration of a disease diagnosis system using a neural network according to an embodiment of the invention.

Referring to FIG. 2, the diagnosis system 100 may include a control module 110, a neural network module 120 in which a neural network is stored, a preprocessing module 130, a heatmap generation module 140, a tissue mask generation module 150, and a visualization module 160. According to one or more embodiments of the invention, some components among the components described above may not necessarily correspond to the components essential to implementation of one or more embodiments of the invention, and in addition, it goes without saying that the diagnosis system 100 may include more components according to embodiments. For example, the diagnosis system 100 may further include a communication module (not shown) for communicating with the client (e.g., 20, 20-1).

The diagnosis system 100 may denote a logical configuration provided with hardware resources and/or software needed to implement one or more embodiments of the invention, and does not necessarily denote a physical component or a device. That is, the diagnosis system 100 may denote a logical combination of hardware and/or software provided to implement one or more embodiments of the invention, and may be implemented as a set of logical components if needed by being installed in the devices separated from each other and performing their functions to implement one or more embodiments of the invention. In addition, the diagnosis system 100 may denote a set of components separately implemented for each function or role for implementing one or more embodiments of the invention. For example, the control module 110, the neural network module 120, the preprocessing module 130, the heatmap generation module 140, the tissue mask generation module 150 and/or the visualization module 160 may be located in different physical devices, or may be located in the same physical device. In addition, according to implementation examples, combinations of software and/or hardware configuring each of the control module 110, the neural network module 120, the preprocessing module 130, the heatmap generation module 140, the tissue mask generation module 150, and/or the visualization module 160 may also be located in different physical devices, and components located in different physical devices may be organically combined with each other to implement each of the modules.

In addition, in this specification, a module may denote a functional or structural combination of hardware for performing one or more embodiments of the invention and software for driving the hardware. For example, those skilled in the art may easily infer that the module may mean a predetermined code and a logical unit of hardware resources for executing the predetermined code, and does not necessarily denote a physically connected code or a single type of hardware.

The control module 110 may control the functions and/or resources of the other components (e.g., the neural network module 120, the preprocessing module 130, the heatmap generation module 140, the tissue mask generation module 150, the visualization module 160, etc.) included in the diagnosis system 100.

The control module 110 may perform patch-level diagnosis according to one or more embodiments of the invention by using the neural network stored in the neural network module 120. As described above, the patch-level diagnosis may be implemented through a deep learning-based neural network according to one or more embodiments of the invention as described above. That is, under the control of the control module 110, the neural network may generate a patch-level diagnosis result indicating whether a disease exists in each of predetermined patches generated by dividing the slide in a predetermined size.

The neural network may denote a set of information expressing a series of design items defining the neural network. In this specification, the neural network may be a convolution neural network.

As is well known in the art, the convolution neural network may include an input layer, a plurality of hidden layers, and an output layer. Each of the plurality of hidden layers may include a convolution layer and a pooling layer (or sub-sampling layer).

The convolution neural network may be defined by functions, filters, strides, weighting factors or the like for defining each of these layers. In addition, the output layer may be defined as a fully connected feedforward layer.

The design details of each layer constituting the convolution neural network are widely known. For example, known functions or functions separately defined to implement one or more embodiments of the invention may be used for the number of layers to be included in the plurality of layers and for each of a convolution function, a pooling function, and an activation function for defining the plurality of layers.

According to an embodiment of the invention, the neural network performing patch-level diagnosis uses a known densenet, and at this point, it may be designed to consider neighboring patches, as well as a specific patch to be diagnosed, as is disclosed in the previous application. In addition, various neural networks may be used, and in any case, the neural network may be defined to receive a specific patch as an input and output a feature value corresponding to the probability of expressing a disease of the specific patch.

The control module 110 may receive input data, i.e., input for each patch, for the neural network stored in the neural network module 120, i.e., a trained neural network. At this point, a value obtained by adding a gray channel value to the original value may be input as described above. It goes without saying that the gray channel value may be obtained by converting a pixel value into a gray value. In addition, an output data, i.e., a feature value corresponding to the probability of expressing a disease corresponding to the patch, may be output by performing operations defined by the neural network. In addition, according to embodiments, the control module 110 may output whether a disease is expressed in a corresponding patch according to whether the feature value is a predetermined threshold value for the sake of the slide-level diagnosis described below.

The neural network module 120 may store a neural network. The neural network may denote a set of information expressing a series of design items defining the neural network. In one or more embodiment, the neural network may be a convolution neural network.

As is well known in the art, the convolution neural network may include an input layer, a plurality of hidden layers, and an output layer. Each of the plurality of hidden layers may include a convolution layer and a pooling layer (or sub-sampling layer).

The convolution neural network may be defined by functions, filters, strides, weighting factors or the like for defining each of these layers. In addition, the output layer may be defined as a fully connected feedforward layer.

The design details of each layer constituting the convolution neural network are widely known in the art. For example, known functions or functions separately defined to implement one or more embodiments of the invention may be used for the number of layers to be included in the plurality of layers and for each of a convolution function, a pooling function, and an activation function for defining the plurality of layers.

An example of the convolution function is a discrete convolution sum. As an example of the pooling function, max pooling, average pooling, or the like may be used. An example of the activation function may be a sigmoid, a tangent hyperbolic (tanh), a rectified linear unit (ReLU), or the like.

When the design items of the convolution neural network are defined, the convolution neural network of which the design items are defined may be stored in the storage device. In addition, when the convolution neural network is trained, a weighting factor corresponding to each layer may be specified.

That is, learning of the convolution neural network may denote a process of determining weighting factors of each layer. In addition, when the convolution neural network is trained, the trained convolution neural network may receive an input data for the input layer and output an output data through the previously defined output layer.

The neural network according to an embodiment of the invention may be defined by selecting any one or a plurality of design items widely known as described above, or independent design items may be defined for the neural network.

The control module 110 may input an input data into the neural network stored in the neural network module 120, i.e., a trained neural network. In addition, it may output an output data by performing the operations defined by the neural network.

The preprocessing module 130 may perform preprocessing on a biometric image needed before performing diagnosis using a neural network. For example, the preprocessing on the biometric image may include a process of tiling the biometric image (i.e., slide) into tiles (patches) of a predefined size, and those skilled in the art may easily infer that appropriate image processing may be performed as needed in a way suitable for the neural network.

Meanwhile, the neural network according to one or more embodiments of the invention has a technical characteristic of including a micro neural network and a macro neural network as described above. This example will be described in detail with reference to FIGS. 4A and 4B.

Figure 4B:
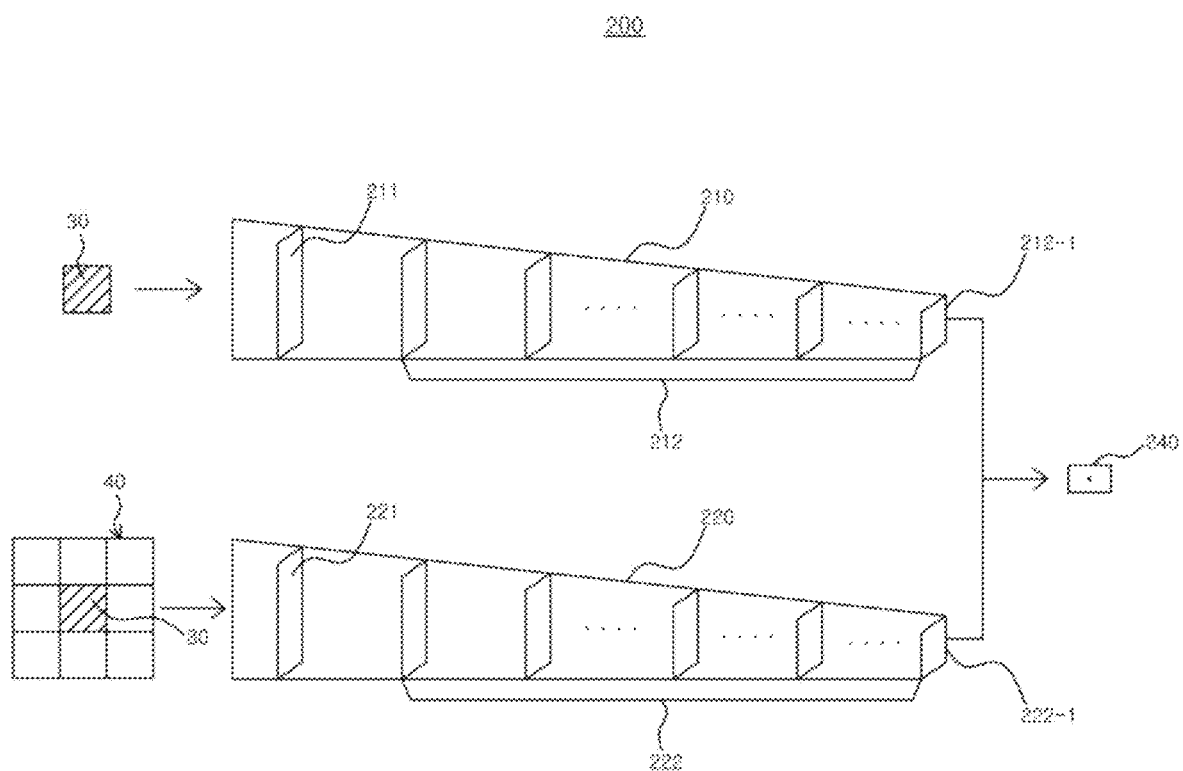

FIGS. 4A and 4B are views showing the configuration of a neural network according to an embodiment of the invention.

Referring to FIGS. 4A and 4B, a neural network 200 according to one or more embodiments of the invention includes a micro neural network and a macro neural network.

The micro neural network includes a plurality of layers 210 and an output layer 230. The plurality of layers 210 include an input layer 211 and a plurality of hidden layers 212.

The macro neural network includes a plurality of layers 220 and an output layer 230. The plurality of layers 220 includes an input layer 221 and a plurality of hidden layers 222.

The micro neural network is defined to receive a specific tile 30 and output a diagnosis result of the specific tile, i.e., output data defined in the output layer 230.

In addition, the macro neural network is defined to receive a macro tile 40 including the specific tile 30 and at least one adjacent tile of the specific tile 30, and output a diagnosis result of the specific tile.

That is, the neural network 200 according to one or more embodiments of the invention may output a diagnosis result considering even the image features of adjacent tiles of the specific tile 30, in addition to image features of the specific tile 30, in order to output the diagnosis result of the specific tile 30.

Although the macro tile 40 in FIGS. 4A and 4B shows an example of using 3×3 tiles surrounding a tile, it goes without saying that various embodiments of macro tiles are possible.

The output layer 230 may receive output data of each of a first immediate-before layer 212-1, which is a layer immediately before the output layer 230 included in the micro neural network, and a second immediate-before layer 222-1, which is a layer immediately before the output layer 230 included in the macro neural network, and output an output data defined in the output layer 230. The first immediate-before layer 212-1, the second immediate-before layer 222-1, and the output layer 230 may be fully connected.

As a feedforward function defining the output layer 230, any one among various functions that output an output data through the output layer 230 as a result of an input data input for the input layer and passing through the neural network 200 may be used.

As a result, in order to perform diagnosis on the specific tile 30, the neural network 200 is trained to output an output data of the output layer 230 corresponding to annotation values of a plurality of training data, considering both the image features of the specific tile 30 and the image features of the macro tile 40 including the specific tile 30.

That is, a plurality of training data is used to train the neural network 200, and the plurality of training data may include a pair of a specific tile 30 and a macro tile 40. In addition, the macro tile 40 may also perform learning by using annotation information of the specific tile 30.

Then, the neural network 200 will be trained to output an output data corresponding to the annotation information of the specific tile 30 considering both the image features of the specific tile 30 and the macro tile 40.

Then, when the trained neural network 200 receives a target tile to be diagnosed and a macro tile corresponding to the target tile as input data of the micro neural network and the macro neural network, it may output a diagnosis result of the target tile, i.e., output data of the output layer 230.

As shown in FIG. 4A, the output layer 230 may output a diagnosis result of the specific patch 30 to be diagnosed as an output data. The diagnosis result may include at least information on the state of a disease of the specific patch 30. The information on the state of a disease may simply signify information on whether a specific disease is expressed in a specific patch 30 (or a probability value). However, depending on the type of a disease, the information on the state of a disease may include information indicating a degree of progression of the disease more specifically.

As disclosed in the previous application, the output layer may be designed to output various additional information, in addition to simply outputting whether or not a disease is expressed. For example, it may include information indicating a degree of progression of a disease and/or related factor information indicating a degree of expression of a related factor related to the value of the state channel. Since this is disclosed in detail in the previous application, detailed description thereof will be omitted for sake of brevity.

When the neural network 200 shown in FIG. 4A is used, although not shown in FIG. 4A, it goes without saying that there may be a layer that receives the output data of the output layer 230 and outputs a feature value corresponding to the probability of expressing a disease of a finally input patch.

Alternatively, as shown in FIG. 4B, the neural network may be designed to have a layer 240 for outputting a feature value corresponding to the probability of expressing a disease of the input patch in substitution for the layer that outputs a plurality of state channels and a related factor channel as shown in FIG. 4A.

According to another embodiment of the invention, the neural network for patch-level diagnosis may be designed to have a single path rather than a method having two paths (paths of a micro network and a macro network) as shown in FIGS. 4A and 4B. This example may be as shown in FIG. 5.

Figure 5:
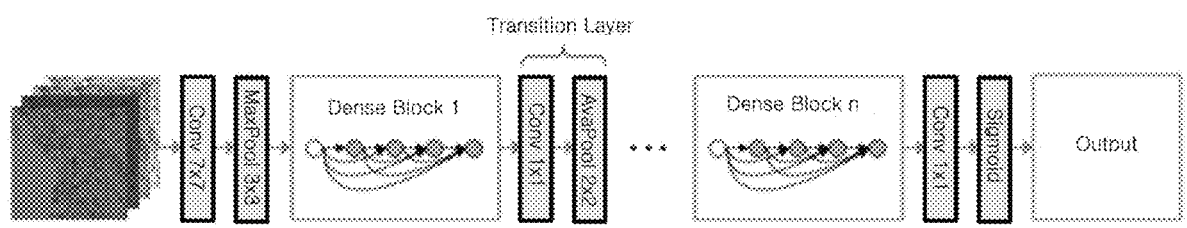
FIG. 5 is a view showing an exemplary configuration of a neural network according to another embodiment.

FIG. 5 is a view showing an exemplary configuration of a neural network according to another embodiment of the invention.

Referring to FIG. 5, as described above, a neural network may be defined to receive an input by the patch and determine whether a disease is expressed in the input patch. At this point, as shown in figure, the neural network may receive 4 channel (e.g., RGB and Gray channels) data.

As shown in FIG. 5, input data may be defined to pass through a convolution layer and a plurality of layers per maxpooling and to output an output data, i.e., whether the input patch is a disease patch. Such a neural network may be a neural network using a known densenet model. In addition, at this point, it can be seen that compared with the original densenet model, 1×1 convolution is added to the neural network according to one or more embodiments of the invention, and there is an effect of confirming an internal feature map. In addition, although a sigmoid function is used as an activation function, various activation functions may be used.

Those skilled in the art may easily infer that a neural network that performs patch-level diagnosis in various other ways may be defined.

On the other hand, according to one or more embodiments of the invention, only tissue parts may be identified and visualized within a patch determined as expressing a disease, and this will be described below in more detail.

Referring to FIG. 2 again, the heatmap generation module 140 may generate a patch-level heatmap image corresponding to the slide on the basis of the patch diagnosis result of each of the plurality of patches included in the slide.

Figure 6A:
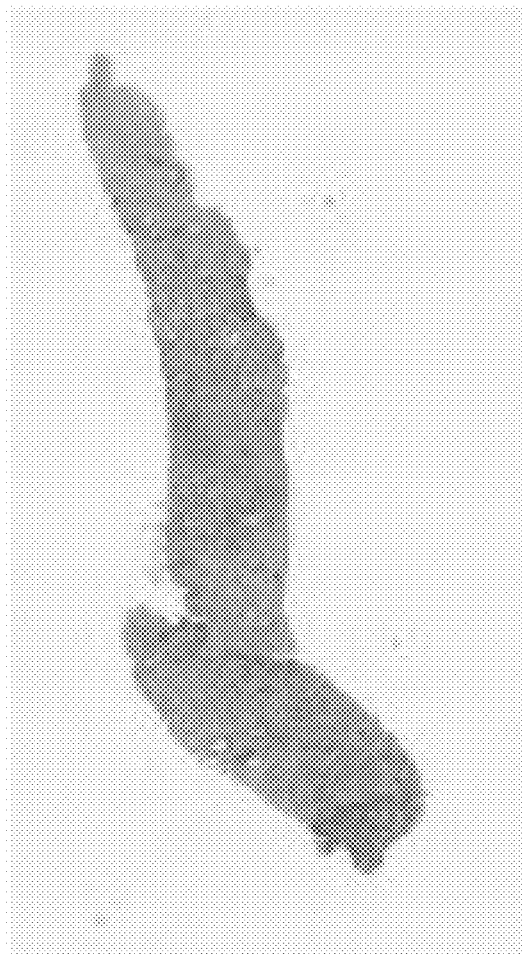
FIG. 6A is a view showing an example of a slide.
Figure 6B:
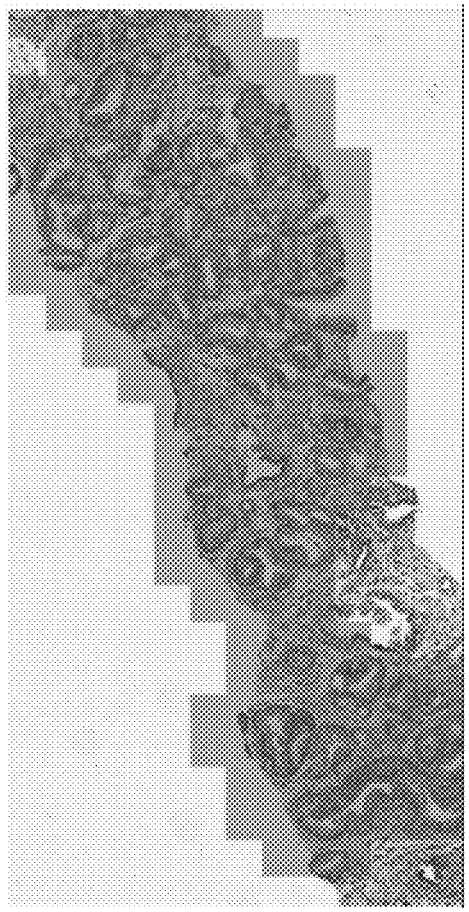
FIG. 6B is a view showing an example of a heatmap for the slide of FIG. 6A.

The heatmap generation module 140 may mark a disease patch according to the diagnosis result of each patch. In the patch-level diagnosis, since each patch is classified according to whether or not there is a disease, the entire disease patch may be marked as a disease. The heatmap generation module 140 may generate a heatmap for the slide as shown in FIG. 6A. For example, the heatmap generation module 140 may generate a heatmap as shown in FIG. 6B. As shown in FIG. 6B, when a patch-level diagnosis result is visualized in the form of a heatmap, a disease part is displayed in a grid form.

Figure 6C:
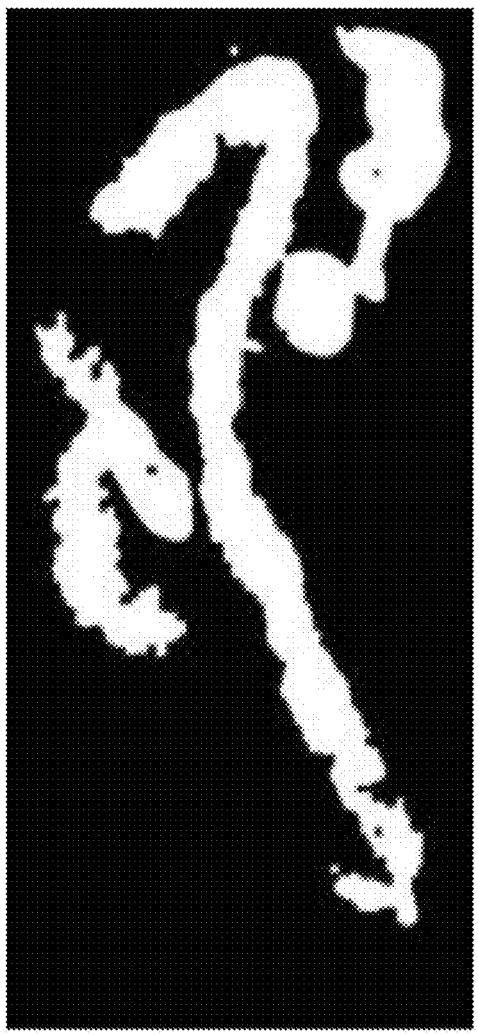
FIG. 6C is a view showing an example of a tissue mask image for the slide of FIG. 6A.

Meanwhile, the tissue mask generation module 150 may generate a tissue mask image for the slide. For example, the tissue mask generation module 150 may generate a tissue mask image as shown in FIG. 6C.

The method of generating a tissue mask image by the tissue mask generation module 150 has the following characteristics.

A more specific description is provided as follows. The tissue mask generation module 150 may generate a tissue mask image corresponding to the slide on the basis of a Hue-Saturation-Value (HSV) model corresponding to the slide.

In an embodiment, the tissue mask generation module 150 may generate a first binarization result by performing image binarization on the S space corresponding to the slide. At this point, the S space corresponding to the slide is a space configured of saturation values of an HSV model corresponding to the slide.

The tissue mask generation module 150 may use Otsu Thresholding as the image binarization method. Otsu Thresholding is a clustering-based image thresholding technique used in the field of computer vision or image processing.

In addition, the tissue mask generation module 150 may generate a second binarization result by performing image binarization on the 1-V space corresponding to the slide. At this point, the V space corresponding to the slide is a space configured of brightness values of an HSV model corresponding to the slide (i.e., having a size of w×h, a matrix configured of the brightness values of the V channel (w is the width of the image, h is the height of the image)), and the 1-V space may be a space subtracting the values of the V channel from a matrix having a size of w×h and filled with 1's.

Meanwhile, the tissue mask generation module 150 may generate a tissue mask image corresponding to the slide on the basis of the first binarization result and the second binarization result.

The first binarization result and the second binarization result may include a binary value (e.g., 0 or 1, or 0 or 255) corresponding to each pixel of the slide, and for each pixel of the slide, the tissue mask generation module 150 may generate a tissue mask image corresponding to the slide by determining a pixel of a tissue mask image corresponding to the pixel as a tissue pixel (a pixel corresponding to the tissue) when the binary value of the first binarization result corresponding to the pixel or the binary value of the second binarization result corresponding to the pixel is 1 (or 255), and determining the pixel of the tissue mask image corresponding to the pixel as a non-tissue pixel (a pixel that does not correspond to a tissue) otherwise (i.e., when the binary value is 0). In summary, the tissue mask generation module 150 may generate a tissue mask image through an OR operation between the image binarization result for the S space and the image binarization result for the 1-V space.

Figure 6D:
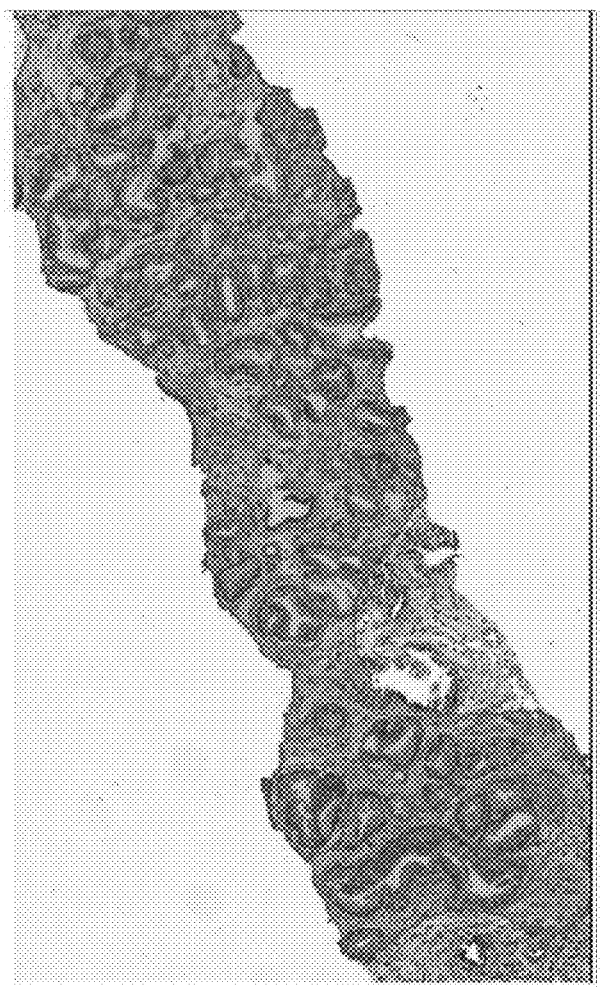
FIG. 6D is a view showing an example of an image as a result of visualizing a part diagnosed as a disease.

Meanwhile, the visualization module 160 may generate a disease diagnosis visualization image corresponding to the slide on the basis of the patch-level heatmap image and the tissue mask image. For example, the visualization module 160 may generate a disease diagnosis visualization image as shown in FIG. 6D.

In an embodiment, the visualization module 160 may generate a disease diagnosis visualization image corresponding to the slide by applying a conditional random field to the patch-level heatmap image and the tissue mask image. Particularly, the conditional random field may be characterized in that the number of labels is 2, and pixels equal to or smaller than a specific threshold among the pixels included in the patch-level heatmap image are converted to 0.

A more detailed description is provided as follows.

The visualization module 160 may receive an original tissue image (i.e., a slide or a patch), a tissue mask image generated by the tissue mask generation module 150, and a patch-level heatmap image generated by the heatmap generation module 140. Describing the size of each input value, since the original tissue image is RGB 3 channels, its size is w×h×3, and the size of the tissue mask image is w×h, and the size of the patch-level heatmap image is also w×h. Meanwhile, the visualization module 160 may convert the w×h patch-level heatmap image into w×h×2. At this point, w×h×[0] contains the original patch-level heatmap image, and w×h×[1] contains each pixel value of a 1 patch-level heatmap image. Then, softmax is taken for dimension=3 to construct a probability space in which each pixel expresses a disease (e.g., prostate cancer), and as the shape of an actual tissue image is affected and transformed by the CRF algorithm according to this probability, the disease image may be visualized to match the shape of the actual tissue.

Particularly, in one or more embodiments of the invention as described herein, the tissue mask generation module 150 may very accurately visualize a part diagnosed as a disease in the slide by simultaneously applying the method of generating a tissue mask image through an OR operation between the image binarization result for the S space and the image binarization result for the 1-V space, and the method of applying the conditional random field.

Comparing FIG. 6D, which is an example of a final visualization result, with FIG. 6B, which is a grid-shaped heatmap, it can be seen that the shape of FIG. 6D is much more clear and easy to discern, and thus make a proper diagnosis of a patient's condition.

Meanwhile, the diagnosis result visualization method according to one or more embodiments of the invention may also be applied to a diagnosis result of a general classification method in which the diagnosis result is derived by the patch. Although even the parts not a tissue are displayed as a disease in the case of patch-unit classification (see FIG. 6A), there is an effect of clearly distinguishing only a tissue part diagnosed as a disease from other parts by applying the diagnosis result visualization method according to one or more embodiments of the invention.

Meanwhile, although an example of applying a system or method according to one or more embodiments of the invention to prostate cancer has been mainly described in this specification, those skilled in the art may easily infer that accurate diagnosis and visualization of a diagnosis result are possible when one or more embodiments of the invention are applied to other diseases that need diagnosis to be performed on a specific tissue considering the state of surrounding tissues of the tissue, as well as the specific tissue.

Meanwhile, according to implementation examples, the diagnosis system 100 may include a processor and a memory for storing programs executed by the processor. The processor may include single-core CPUs or multi-core CPUs. The memory may include high-speed random-access memory and may include one or more non-volatile memory devices such as magnetic disk storage devices, flash memory devices, and other non-volatile solid state memory devices. Access to the memory by the processor and other components may be controlled by a memory controller.

Meanwhile, the diagnosis method through a neural network according to an embodiment of the present invention may be implemented in the form of a computer-readable program command and stored in a computer-readable recording medium, and control programs and target programs according to an embodiment of the present invention may also be stored in the computer-readable recording medium. The computer-readable recording medium includes all types of recording devices for storing data that can be read by a computer system.

One or more embodiments of the invention as described herein may be used in a system and method for diagnosing a disease using a neural network.

The program commands recorded in the recording medium may be specially designed and configured for the present invention, or may be known to and used by those skilled in the software field.

Examples of the computer-readable recording medium include magnetic media such as hard disks, floppy disks, and magnetic tapes, optical media such as CD-ROMs and DVDs, magneto-optical media such as floptical disks, and hardware devices specially configured to store and execute program commands, such as ROM, RAM, flash memory and the like. In addition, the computer-readable recording medium may be distributed in computer systems connected through a network to store and execute computer-readable codes in a distributed manner.

Examples of program instructions include high-level language codes that can be executed by a device that electronically processes information using an interpreter or the like, e.g., a computer, as well as machine language codes such as those produced by a compiler.

The hardware device described above may be configured to execute as one or more software modules to perform the operation of the present invention, and vice versa.

The above description of the present invention is for illustrative purposes, and those skilled in the art may understand that it is possible to easily transform into other specific forms without changing the spirit or essential features of the present invention. Therefore, it should be understood that the embodiments described above are illustrative and non-limiting in all respects. For example, each component described as a single form may be implemented in a distributed manner, and in the same manner, components described as being distributed may also be implemented in a combined form.

The scope of the present invention is indicated by the claims described below rather than the detailed description, and the meaning and scope of the claims and all changes or modified forms derived from the equivalent concepts thereof should be interpreted as being included in the scope of the present invention.

The invention claimed is:

1. A disease diagnosis system implemented in a system including a processor and a storage device for storing a neural network, and using a biometric image obtained from a biological sample provided on a slide, and the neural network, the diagnosis system comprising:
the neural network configured to generate a patch-level diagnosis result indicating whether a disease exists in each of predetermined patches generated by dividing the biometric image obtained from the slide in a predetermined size, the biometric image being divided and processed by the neural network: a) receiving the biometric image that includes three channels of RGB color data values for each of a plurality of pixels, and b) receiving, on a fourth channel, an input value for each pixel included in the plurality of patches, wherein the fourth channel comprises a gray data value of each pixel in the plurality of patches;
a heatmap generation module configured to generate a patch-level heatmap image corresponding to the slide on the basis of the patch-level diagnosis result of each of the plurality of patches included in the slide;
a tissue mask generation module configured to generate a tissue mask image corresponding to the biometric image obtained from the slide on the basis of a hue-saturation-value (HSV) model corresponding to the biometric image obtained from the slide; and a visualization module configured to generate a disease diagnosis visualization image corresponding to the biometric image obtained from the slide on the basis of the patch-level heatmap image and the tissue mask image,
wherein the neural network comprises:
a micro neural network using training data for a specific tile; and
a macro neural network using training data for a micro tile including the specific tile and at least one adjacent tile of the specific tile.

2. The system according to claim 1, wherein the tissue mask generation module generates a first binarization result by performing image binarization on an S space corresponding to the biometric image obtained from the slide, generates a second binarization result by performing image binarization on a 1-V space corresponding to the biometric image obtained from the slide, and generates a tissue mask image corresponding to the biometric image obtained from the slide on the basis of the first binarization result and the second binarization result.

3. The system according to claim 2, wherein the first binarization result and the second binarization result include a binary value corresponding to each pixel of the biometric image obtained from the slide, wherein the binary value is 0 or 1, and
for each pixel of the biometric image obtained from the slide, the tissue mask generation module determines a pixel of a tissue mask image corresponding to the pixel as a tissue pixel when the binary value of the first binarization result corresponding to the pixel or the binary value of the second binarization result corresponding to the pixel is 1, and determines the pixel of the tissue mask image corresponding to the pixel as a non-tissue pixel otherwise.

4. The system of claim 2, wherein the S space corresponding to the biometric image obtained from the slide is a saturation space of an HSV model corresponding to the slide.

5. The system of claim 4, wherein the V space corresponding to the biometric image obtained from the slide is a brightness value space of an HSV model corresponding to the slide.

6. The system according to claim 1, wherein the visualization module generates a disease diagnosis visualization image corresponding to the biometric image obtained from the slide by applying a Conditional Random Field to the patch-level heatmap image and the tissue mask image.

7. The system according to claim 6, wherein in the conditional random field, the number of labels is 2, and pixels equal to or smaller than a specific threshold among the pixels included in the patch-level heatmap image are converted to 0.

8. The system according to claim 1, wherein the disease is prostate cancer.

9. A method performed by a disease diagnosis system implemented in a system including a processor and a storage device and using a biometric image and a neural network, the method comprising:
a diagnosis step of generating a patch-level diagnosis result indicating whether a disease exists in each of predetermined patches generated by dividing a biometric image obtained from a slide in a predetermined size using the neural network, by the diagnosis system, the biometric image being divided and processed by the neural network: a) receiving the biometric image that includes three channels of RGB color data values for each of a plurality of pixels, and b) receiving, on a fourth channel, an input value for each pixel included in the plurality of patches, wherein the fourth channel comprises a gray data value of each pixel in the plurality of patches;
a heatmap generation step of generating a patch-level heatmap image corresponding to the biometric image obtained from the slide on the basis of the patch-level diagnosis result of each of the plurality of patches included in the biometric image obtained from the slide, by the diagnosis system;
a tissue mask generation step of generating a tissue mask image corresponding to the biometric image obtained from the slide on the basis of a hue-saturation-value (HSV) model corresponding to the biometric image obtained from the slide, by the diagnosis system; and
a visualization step of generating a disease diagnosis visualization image corresponding to the biometric image obtained from the slide on the basis of the patch-level heatmap image and the tissue mask image, by the diagnosis system,
wherein:
the neural network comprises a micro neural network and a macro neural network; and
the method further comprises a step of training the neural network to more optimally process biometric images by using a plurality of training data that include a specific tile of the micro neural network and a macro tile of the macro neural network, the macro tile including the specific tile and at least one adjacent tile of the specific tile.

10. The method according to claim 9, wherein the tissue mask generation step includes the steps of:
generating a first binarization result by performing image binarization on an S space corresponding to the biometric image obtained from the slide;
generating a second binarization result by performing image binarization on a 1-V space corresponding to the biometric image obtained from the slide; and generating a tissue mask image corresponding to the biometric image obtained from the slide on the basis of the first binarization result and the second binarization result.

11. The method according to claim 10, wherein the first binarization result and the second binarization result include a binary value corresponding to each pixel of the biometric image obtained from the slide, wherein the binary value is 0 or 1, and the step of generating a tissue mask image corresponding to the biometric image obtained from the slide on the basis of the first binarization result and the second binarization result includes the step of determining, for each pixel of the biometric image obtained from the slide, a pixel of a tissue mask image corresponding to the pixel as a tissue pixel when the binary value of the first binarization result corresponding to the pixel or the binary value of the second binarization result corresponding to the pixel is 1, and determining the pixel of the tissue mask image corresponding to the pixel as a non-tissue pixel otherwise.

12. The method according to claim 9, wherein the visualization step includes the step of generating a disease diagnosis visualization image corresponding to the biometric image obtained from the slide by applying a Conditional Random Field to the patch-level heatmap image and the tissue mask image.

13. The method according to claim 12, wherein in the conditional random field, the number of labels is 2, and pixels equal to or smaller than a specific threshold among the pixels included in the patch-level heatmap image are converted to 0.

14. The method of claim 10, wherein the S space corresponding to the biometric image obtained from the slide is a saturation space of an HSV model corresponding to the biometric image obtained from slide.

15. The method of claim 14, wherein the V space corresponding to the biometric image obtained from the slide is a brightness value space of an HSV model corresponding to the biometric image obtained from the slide.

16. The method of claim 9, wherein the learning is further performed using annotation information of the specific tile.

17. A computer program installed in a data processing apparatus and recorded in a non-transitory computer readable medium for performing the method disclosed in claim 9.

* * * * *